(12) United States Patent
Small et al.

(10) Patent No.: US 6,461,831 B1
(45) Date of Patent: Oct. 8, 2002

(54) DIAGNOSTIC TEST FOR ALZHEIMER'S DISEASE

(76) Inventors: David Henry Small, 35 Munro Ave., Ashburton, Victoria 3147 (AU); Javier Saez-Valero, Flat 67, 50 King William Street, Fitzroy Victoria 3065 (AU); Gian Sberna, 18 Bath Road, Burwood, Victoria 3125 (AU)

( * ) Notice: Subject to any disclaimer, the term of this patent is extended or adjusted under 35 U.S.C. 154(b) by 0 days.

(21) Appl. No.: 09/509,203

(22) PCT Filed: Sep. 24, 1998

(86) PCT No.: PCT/AU98/00809

§ 371 (c)(1),
(2), (4) Date: Sep. 21, 2000

(87) PCT Pub. No.: WO99/15695

PCT Pub. Date: Apr. 1, 1999

(30) Foreign Application Priority Data

Sep. 24, 1997 (AU) ............................................. P09432

(51) Int. Cl.$^7$ ............................ C12Q 1/46; C12Q 1/44; C12N 1/00; G01N 33/53

(52) U.S. Cl. ........................... 435/20; 435/19; 435/827; 435/7.1

(58) Field of Search ............................ 435/20, 19, 827, 435/7.1

(56) References Cited

U.S. PATENT DOCUMENTS 5,200,324 * 4/1993 Navaratnam et al.
5,595,883 * 1/1997 Appleyard et al.

FOREIGN PATENT DOCUMENTS

EP 0 474 190 A1 3/1992

OTHER PUBLICATIONS

Tornel et al. (1992). Ricinus commnuis agglutinin I reacting and non–reacting butyrylcholinesterase in human cerebrospinal fluid. Neuroscience Letters 145, pp. 59–62.*
Mimori et al. (1997). Abnormalities of acetylcholinesterase in Alzheimer's disease with special reference to effect of acetylcholinesterase inhibitor. Behavioural Brain Research 83(1–2), pp. 25–30.*
Kalaria et al. (1992). Acetylcholinesterase and its association with heparan sulfphate proteoglycans in cortical amyloid deposits of Alzheimer's Disease. Neuroscience 51(1), pp 177–184.*
Cabezas–Herrera et al., "$G_4$ Forms of Acetylcholinesterase and Butyrylcholinesterase in Normal and Dystrophic Mouse Muscle Differ in Their Interaction with *Ricinus communis* Agglutinin" *Biochimica et Biophysica Acta* 1225:283–288 (1994).

Inestrosa et al., "Monomeric Amphiphilic Forms of Acetylcholinesterase Appear Early During Brain Development and May Correspond to Biosynthetic Precursors of the Amphiphilic $G_4$ Forms" *Neuroscience Letters* 173:155–158 (1994).

Navaratnam et al., "Anomalous Molecular Form of Acetylcholinesterase in Cerebrospinal Fluid in Histologically Diagnosed Alzheimer's Disease" *The Lancet* 337:447–449 (1991).

Saez–Valero et al., "Glycosylation of Acetylcholinesterase as Diagnostic Marker for Alzheimer's Disease" *The Lancet* 350:929 (1997).

Shen et al., "Anomalous Acetylcholinesterase in CSF Without Clinical Diagnosis of Alzheimer's Disease" *The Lancet* 342:62 (1993).

Siek et al., "Molecular Forms of Acetylcholinesterase in Subcortical Areas of Normal and Alzheimer Disease Brain" *Biol. Psychiatry* 27:573–580 (1990).

Smith et al., "Anomalous Acetylcholinesterase in Lumber CSF in Alzheimer's Disease" *The Lancet* 338:1538 (1991).

* cited by examiner

Primary Examiner—Ralph Gitomer
Assistant Examiner—Mahreen Chaudhry
(74) Attorney, Agent, or Firm—Clark & Elbing LLP

(57) ABSTRACT

A method for the diagnosis of Alzheimer's disease (AD) in a patient, comprising the steps of: (1) providing a sample of an appropriate body fluid from said patient; (2) detecting the presence of acetylcholinesterase (AChE) with an altered glycosylation pattern in said sample. It has been established that approximately 75–95% of the AChE in the CSF of AD patients binds to Concanavalin (Con A) or wheat germ agglutinin (WGA) but with different specificity to each. Accordingly, in order to identify the glycosylation pattern of AChE in the sample, the binding to Con A is determined, then the binding to WGA is determined, and a ratio calculated. The ratio is characteristic of the glycosylation pattern. In alternative embodiment of the invention a monoclonal antibody specific for AChE with an altered glycosylation pattern is used to detect its presence.

18 Claims, 6 Drawing Sheets

DIAGNOSTIC TEST FOR ALZHEIMER'S DISEASE

TECHNICAL FIELD

The present invention is concerned with a diagnostic test for Alzheimer's disease.

BACKGROUND ART

Alzheimer's disease (AD) is a common progressive dementia involving loss of memory and higher cognitive function. The disease is characterized by the presence of amyloid deposits in the brains of sufferers. These deposits are found both extracellularly (amyloid plaques) and intracellularly (neurofibrillary tangles). The principal constituent of amyloid plaques is the amyloid protein (A$\beta$) which is produced by proteolytic cleavage for the amyloid protein precursor (APP) (Evin et al., 1994). The principal constituent of neurofibrillary tangles is the cytoskeletal protein tau (Kosik, 1992).

One of the characteristic neurochemical changes observed in AD is the loss of acetylcholinesterase (AChE) and choline acetyltransferase activity in regions of the brain such as the cortex, hippocampus, amygdala and nucleus basalis (Whitehouse et al., 1981, 1982; Struble et al., 1982; Mesulam and Geula, 1988). The loss of cholinergic structure and markers correlates with the number of plaque and tangle lesions present, as well as with the clinical severity of the disease (Perry et al., 1978; Wilcock et al., 1982; Neary et al., 1986; Perry, 1986).

Accurate diagnosis of AD during life is essential. However, clinical evaluation is at best only about 80% accurate. Therefore, there is a need to identify specific biochemical markers of AD. So far, analysis of blood or cerebrospinal fluid (CSF) has not yielded a biochemical marker of sufficient diagnostic value (Blass et al., 1998), although detectable differences are reported in the levels of certain proteins (Motter et al., 1995).

The assay of levels of AChE activity in the blood and the cerebrospinal fluid (CSF) has been proposed as an ante mortem diagnostic test for AD. However, no consensus has been reached as to whether the levels of AChE are consistently affected in these tissues. The level of serum or plasma AChE has been reported to be increased (Perry et al., 1982; Atack et al., 1985), decreased (Nakano et al., 1986; Yamamoto et al., 1990) or unchanged (St. Clair et al., 1986; Sirvio et al., 1989) in AD patients. The level of erythrocyte AChE has been reported as either unaffected (Atack et al., 1985; Perry et al., 1982) or decreased (Chipperfield et al., 1981). The level of AChe activity in the CSF of AD patients has been reported to be decreased (most recently by Appleyard and McDonald, 1992; Shen et al., 1993) or unchanged (most recently by Appleyard et al., 1987; Ruberg et al., 1987).

AChE has been shown to exist as up to six different molecular isoforms, three of which are the monomeric (G1), dimeric (G2) and tetrameric (G4) isoforms (Massoulie et al., 1993). The relative proportion of the different isoforms of AChE are markedly affected in AD, with a decrease in the G4 isoform in the parietal cortex (Atack et al., 1983), and an increase in the G1 isoform (Arendt et al., 1992). Similar changes have been identified in other AD brain regions including Brodman areas 9, 10, 11, 21 and 40, as well as the amygdala (Fishman et al., 1986). Asymmetric collagen-tailed isoforms (A12) are increased by up to 400% in Brodman area 21, although they represent only a trace amount of the total AChE in the human brain (Younkin et al., 1986).

However, to date changes in AChE expression and isoform distribution have not been found to be of sufficient sensitivity or specificity to be useful diagnostic markers of AD.

An anomalous isoform of AChE, distinguished by its isoelectric point, has been detected in the CSF of AD patients (Havaratnam et al., 1991; Smith et al., 1991), and a method for screening for AD based on these findings is described in U.S. Pat. No. 5,200,324. The method comprises determining, by means of isoelectric focusing, if a patient has an anomalous form of AChE in his CSF. However, the isoform detected by Navaratnam et al and Smith et al has also been detected in the CSF of patients with other neurological diseases (Shen and Zhang, 1993). Indeed, this is suggested in U.S. Pat. No. 5,200,324 at column 7 lines 19–22, where it is stated that the anomalous AChE "was present in the CSF of four out of eight patients with a clinical diagnosis of possible dementia, but who did not satisfy strict histopathological criteria for Alzheimer's disease".

Moreover, the passage at column 7 lines 60–61 of the US patent indicates that the detection of AChE-AD in lumbar CSF depends upon the amount of CSF analysed, and column 8 lines 38–40 state that the anomalous band was often rather faint and the gels run were not always ideal. Accordingly, a loading of 5 mU per track was adopted as a standard procedure for screening CSF for the presence of the anomalous form of AChE, and each gel was read independently by four individuals who recorded their interpretation. Thus, there are technical problems associated with the assay described which can only be overcome by adopting an arbitrary set of conditions to avoid false readings, which then makes interpretation of the results difficult.

The suggestion that the anomalous form of AChE detected by Navaratnam et al and Smith et al is not unique to AD patients, together with the technical problems associated with the assay described in U.S. Pat. No. 5,200,324 suggests that the abnormal electroform of AChE discovered by Navaratnam et al and Smith et al will not form the basis of a diagnostic test for AD suitable for clinical use.

DISCLOSURE OF THE INVENTION

There remains a need for a diagnostic test for AD based on a biochemical analysis of body fluids such as blood or CSF and the present invention provides such a test on the basis that the AChE of AD patients shows a different glycosylation pattern to the AChE of non-AD groups.

According to a first aspect of the present invention there is provided a method for the diagnosis of Alzheimer's disease (AD) in a patient, comprising the steps of:

(1) providing a sample of an appropriate body fluid from said patient;

(2) detecting the presence of acetylcholinesterase (AChE) with an altered glycosylation pattern in said sample.

In one embodiment of the invention the relative proportion of AChE with a first glycosylation pattern and AChE with a second glycosylation pattern is measured.

Measurement of the relative proportions of AChE with first and second glycosylation patterns may be carried out in any convenient manner, for example, by using biochemical analysis techniques such as HPLC and mass spectrometry, or immunological techniques such as ELISA or, assays. However, a particularly preferred means of measuring the relative proportions of the isoforms of AChE involves a lectin-binding analysis.

It has been established that approximately 75%–95% of the AChE in the CSF of AD patients binds to Concanavalin A (Con A) or to wheat germ agglutinin (WGA), but with different specificity to each. Accordingly, in a particularly preferred embodiment of the invention, in order to identify the glycosylation pattern of AChE in the sample, the binding to Con A is determined, then the binding to WGA is determined, and a ratio calculated. The ratio is characteristic of the glycosylation pattern. It is particularly convenient to measure the activity of unbound AChE in each experiment, hence the ratio of AChE unbound to Con A to the ratio of AChE unbound to WGA is determined. This ratio is referred to hereinafter as a C/W ratio. For patients with AD, the C/W ratio has generally been found to be above 0.95, whereas for non-sufferers of AD the C/W ratio is typically below 0.95. In an alternative embodiment of the invention a monoclonal antibody specific for AChE with an unaltered glycosylation pattern is used to detect its presence. Typically the monoclonal antibody is MA3-042 (clone HR2), available from Chemicon International Inc of Temecula, Calif. Other suitable monoclonal antibodies may be used, for example, MA304 (clone AE1) also available from Chemicon International Inc.

While not wishing to be bound by theory, it is believed that the abnormal isoform is the amphiphilic, monomeric isoform of AChE and/or the amphiphilic, dimeric isoform of AChE.

The body fluid analysed can be cerebrospinal fluid (CSF), blood or blood plasma. Advantageously, when said body fluid is blood, blood plasma is prepared from the blood for analysis. The blood plasma is treated to remove or inactivate butyrylcholinesterase (BChE) prior to analysis.

According to a second aspect of the present invention there is provided an abnormal isoform of the acetylcholinesterase (AChE) with an altered pattern of glycosylation, being the amphiphilic, monomeric isoform of AChE and characterised in that it has a relatively lesser affinity for Concanavalin A (Con A) and a relatively greater affinity for wheat germ agglutinin (WGA) than AChE with an unaltered glycosylation pattern.

According to a third aspect of the present invention there is provided an abnormal isoform of the acetylcholinesterase (AChE) with an altered glycosylation pattern, being the amphiphilic, dimeric isoform of AChE and characterised in that it has a relatively lesser affinity for Concanavalin A (Con A) and a relatively greater affinity for wheat germ agglutinin (WGA) than AChE with an unaltered glycosylation pattern.

BEST MODE FOR CARRYING OUT THE INVENTION

Figure 1:
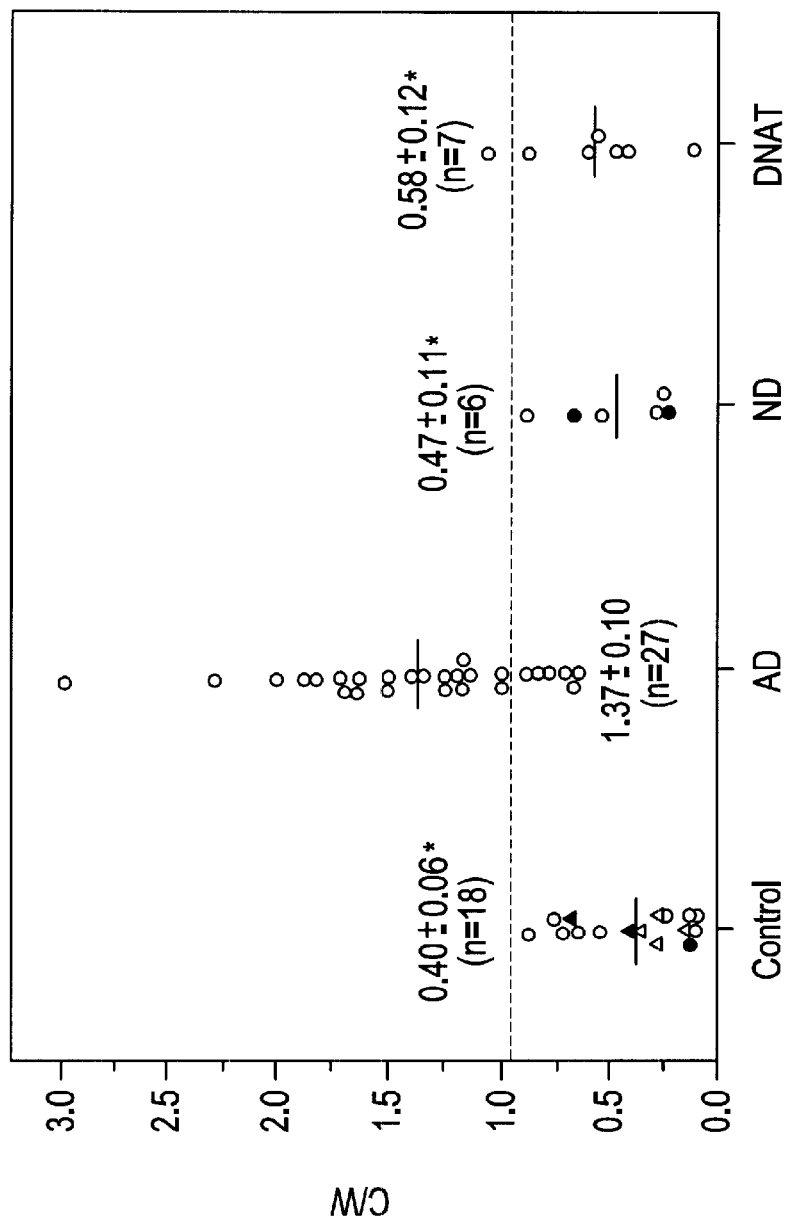
FIG. 1 is a plot of the C/W ratio for a number of patients in a control group, patients with Alzheimer's disease (AD), patients with other neurological disorders distinct from Alzheimer's disease (ND) and patients with non-Alzheimer's disease type dementia (DNAT). Circles represent ventricular CSF; triangles represent lumbar CSF; open symbols=$\geq$60 years old; black symbols=$\leq$60 years old. Mean values are expressed±S.E.M.*=significantly different from AD (P<0.001). The dashed line represents the value of C/W which maximally discriminates between AD and non-AD groups. The experiment is described in Example 1.

Abbreviations Used:

AChE, acetylcholinesterase; ChE, cholinesterase; Aβ, amyloid β protein; AD, Alzheimer's disease; DP, diffuse plaques; ND, other neurological diseases; PMI, post mortem interval; PBS, phosphate-saline buffer; TB, Tris buffer; TSB, Tris-saline buffer; SS, salt-soluble supernatant; TS, Triton X-100-soluble supernatant; AF, amphiphilic fraction; EF, hydrophilic fraction; $G^a$, globular amphiphilic isoform; $G^{na}$, globular non-amphiphilic isoform; and agglutinins from *Canavalia ensiformis* (Concanavalin A), Con A; *Triticum vulgaris* (wheat germ), WGA; *Ricinus communis*, $RCA_{120}$; *Lens culinaris*, LCA; *Dolichus biflorus*, DBA; *Ulex europaeus*, $URA_I$; *Glycine max*, SBA; and *Arachis hypogaea*, PNA.

Materials

Immobilised lectins (Con A- and LCA-Sepharose, WGA-, RCA$_{120}$-, DBA-, UEA$_I$-, SBA and PNA-agarose), phenylagarose, bovine liver catalase, *E. coli* alkaline phosphatase, polyoxyethylene-10-oleyl ether (Brij 97), Triton X-100, tetraisopropyl pyrophosphoramide (iso-OMPA), 1,5-bis(4-allydimethyl-ammoniumphenyl)-pentan-3-dibromide (BW284c51), acetyithiocholine iodide and 5,5'-dithio-bis-2-nitrobenzoiclacid (DTNB) were all obtained from Sigma-Aldrich Pty. Ltd. (Seven Hills, NSW, Australia). Sepharose CL-4B was purchased from Pharmacia Bioteh AB (Uppsala, Sweden).

EXAMPLE 1

Lectin Binding Experiments in AD Patients

Lumbar or ventricular CSF was obtained post mortem; 18 controls with no clinical or pathological dementia and no clinical or pathological dementia and no evidence of brain pathology, 27 cases of AD, 7 cases of dementia non-AD type (DNAT, 5 frontal lobe dementia, 1 Lewy body dementia/Parkinson's disease and 1 multi-infarct dementia/congophilic amyloid angiopathy), and 6 cases of other neurological disorders (ND, 4 Huntington's disease, 1 schizophrenia and 1 corticobasal degeneration). The average age in the control group was 68±4 years, there were 10 females and 8 males and the PMI was 40±6. In the AD group the age was 81±2 years, there were 13 female and 14 males and the PMI was 35±6. in the ND group the age was 65±6, there were 3 females and 3 males and the PMI was 45±12. In the DNAT group the age was 76±3, there were 4 female and 3 males and the PHI was 34±11. Samples of CSF were stored at −70° C. and centrifuged at 1,000×g for 15 min prior to analysis. AChE activity was assayed at 22° C. by a modified microassay of the Ellman method (Ellman et al. 1961). Aliquots (0.3 ml) were mixed with 0.1 ml of Sepharose 4B in PBS (control), concanavalin A (Con A) or wheat germ agglutinin (WGA, *Triticum vulgaris*) immobilised on Sepharose. The enzyme-lectin mixture was incubated overnight at 4° C., and then centrifuged (1,000×g, 15 min). AChE activity was assayed in the supernatant fractions. Data were analysed using a Student's t-test.

The total AChE values in ventricular CSF samples of subjects ≧60 yrs old were significantly lower in the AD group (6.98±0.82 nmol/min/ml) than in controls (17.24±4.28 nmol/min/ml; P<0.001). However, as reported previously, (Appleyard et al., 1983), the large overlap (40%) between the data prevents the use of total AChE as a significant diagnostic marker.

However, lectin-binding analysis revealed a significant difference between the AD group and controls. Approximately 75–95% of the AChE in the CSFs bound to Con A or WGA. A ratio (C/W ratio) was defined as AChE unbound to Con A divided by AChE unbound to WGA. The mean C/W ratio for the AD group was significantly different from controls (FIG. 1). Of the 27 CSFs from confirmed AD, 21 samples had a C/W ratio >0.95. All 18 control samples had C/W <0.95, without significant differences between younger (n=5, C/W=0.37±0.10) and older subjects (n=6, 0.38±0.08) samples. No correlation in C/W ratio was noted with post mortem interval (PMI). The data are represented graphically in FIG. 1.

The data indicate that lectin-binding analysis of CSF AChE could provide a diagnostic test for AD which is 80% sensitive and 97% specific. Thus it was proposed that differences observed in the glycosylation pattern of AChE in CSF may be useful as an ante mortem diagnostic marker for AD, particularly when used in combination with measurement of other biochemical markers.

EXAMPLE 2

Further Lectin Binding Experiments

Experimental Procedures

Human Brain and CSF Samples

Ventricular and lumbar CSF, frontal cortical and cerebellar samples were obtained post mortem and stored at −80° C. Three non-AD groups of samples were defined, 1) controls with no clinical or pathological features of dementia (n=18), 2) individuals who showed no clinical signs of dementia but who were found to have a moderate number of non-neuritic Ab-immunoreactive diffuse plaques (DP), but no evidence of neocortical neurofibrillary changes (n=6), and 3) individuals with various neurological diseases (ND) containing 7 cases of non-AD type dementia (5 frontal lobe dementia, 1 Lewy body dementia and 1 vascular dementia) and 7 cases of other neurological disorders (4 Huntington's disease, 1 Parkinson's disease, 1 schizophrenia and 1 corticobasal degeneration). Cases of AD were selected on the basis of their clinical history of dementia and neuropathological CERAD diagnosis (Mirra et al., 1994). All the CSF samples included in the AD and ND groups were ventricular and only 5 control and 1 DP CSF samples (from a total of 18 and 6 subjects, respectively) were taken by lumbar puncture. Immunohistochemical examination of the cerebellar samples showed that, unlike the frontal cortex, none of the AD tissue possessed compact neuritic amyloid plaque deposition (data not shown), consistent with previous studies (Mann et al., 1996).

It has been shown (Grassi et al., 1982; Fishman et al., 1986; Sáez-Valero et al., 1993) that for a post mortem interval (PMI) greater than 72 hr. storage at −20° C. or repeated cycles of freeze-thawing caused degradation of AChE, which confounded glycosylation analysis. Therefore, only samples with a PMI of less than 72 hr (PMI=36±4 hr) were used. There was no significant difference in PMI between each group of samples.

Preparation of Samples and Extraction of AChE

Samples of CSF were thawed slowly at 4° C. and then centrifuged at 1,000×g for 15 min prior to use. Small pieces (0.5 g) of frontal cortex and cerebellum were thawed slowly at 4° C., weighed and homogenised (10% w/v) in ice-cold Tris-saline buffer (TSB; 50 mM Tris-HCl, 1 M NaCl, and 50 mM MgCl$_2$, pH 7.4) containing a cocktail of proteinase inhibitors (Silman et al., 1978). Tissues were homogenised with a glass/Teflon homogeniser and then sonicated with 10–15 bursts at 50% intermittency at setting 4 using a Branson sonifier. The suspension was centrifuged at 100,000×g at 4° C. in a Beckman L8-80M ultracentrifuge using a 70.1 Ti rotor for 1 hr to recover a salt-soluble ChE fraction (SS). The pellet was re-extracted with an equal volume of TSB containing 1% (w/v) Triton X-100, and the suspension centrifuged at 100,000×g at 4° C. for 1 hr to obtain a Triton X-100-soluble ChE fraction (TS). This double-extraction method recovered 80–90% of the total ChE activity (S áez-Valero et al., 1993; Moral-Naranjo et al., 1996).

AChE Assay and Protein Determination

AChE activity was determined by a modified microassay method of Ellman (Sáez-Valero et al., 1993). One unit of AChE activity was defined as the number of nmoles of acetylthiocholine hydrolysed per min at 22° C. Protein concentrations were determined using the bicinchoninic acid method with bovine serum albumin as standard (Smith et al., 1985).

Hydrophobic Interaction Chromatography on Phenyl-agarose

Amphiphilic AChE forms were separated from hydrophilic forms by hydrophobic interaction chromatography on phenyl-agarose as previously described (Sáez-Valero et al., 1993). CSF (10 ml-pooled from four samples obtained from four different subjects) was applied to a column (10×1 cm)

of phenyl-agarose. A hydrophilic fraction (HF) containing hydrophilic isoforms of AChE was eluted with 30 ml of TSB, and then an amphiphilic fraction (AF) containing bound amphiphilic isoforms was eluted with 50 mM Tris-HCl (TB, pH 7.4) containing 2% (w/v) Triton X-100. Peak fractions with high AChE activity were pooled and concentrated using Ultrafree-4 Centrifugal Filter Device Biomax 10 kDa concentrators (Millipore Corporation, Bedford, Mass., USA).

Sedimentation Analysis

Molecular isoforms of AChE were analyzed by ultracentrifugation at 150,000×g in a continuous sucrose gradient (5–20% w/v) for 18 hr at 4° C. in a Beckman SW40 rotor. The gradients contained 10 ml of 50 mM Tris-HCl (pH 7.4) containing 0.5 M NaCl, 50 mM $MgCl_2$ and 0.5% (w/v) Brij 97. Approximately 40 fractions were collected from the bottom of each tube. Enzymes of known sedimentation coefficient, bovine liver catalase (11.4S, $S_{20,w}$, Svedberg Units) and E. coli alkaline phosphatase (6.1S) were used in the gradients to determine the approximate sedimentation coefficients of AChE isoforms. A ratio of AChE species $G_4/(G_2+G_1)$, that reflected the proportion of $G_4$ molecules ($G_4^{na}+G_4^a$) versus both light globular AChE isoforms, $G_2^a$ and $G_1^a$ was defined. Estimation of the relative proportions of each molecular form of AChE was performed by adding the activities under each peak ($G_4$ or $G_2+G_1$) and calculating the relative percentages (recovery >95%).

Lectin-binding Analysis of AChE

Samples (0.3 ml) were added to 0.1 ml (hydrated volume) of Sepharose 4B (control), Con A, WGA, $RCA_{120}$, LCA, DBA, $UEA_I$, SBA or PNA immobilised in agarose or Sepharose. The enzyme-lectin mixture was incubated overnight at 4° C. with gentle mixing. Bound and free AChE were separated by centrifugation at 1000×g for 15 min at 4° C. in a Beckman J2-21M/E centrifuge using a JA-20 rotor, and the unbound AChE was assayed in the supernatant fraction. Percentage of unbound AChE in the lectin incubation was calculated as (AChE unbound to lectin/AChE unbound to Sepharose)×100. The C/W ratio was calculated according to the formula, AChE activity unbound in the Con A incubation divided by the AChE activity unbound in the WGA incubation. it was observed that this ratio detects a specific alteration in AChE glycosylation that occurs in AD CSF.

Lectin Binding of CSF AChE

To examine the glycosylation of ACE, CSF samples from 18 controls and 30 cases of AD were incubated with different imobilised lectins, which recognise different sugars. AChE bound strongly to Con A, WGA and LCA but weakly to $RCA_{120}$, PNA, DBA, URA, and SBA (Table 1), suggesting that most of the enzyme was devoid of terminal galactose, terminal N-acetyl-galactosamine or fucose.

Figure 2:
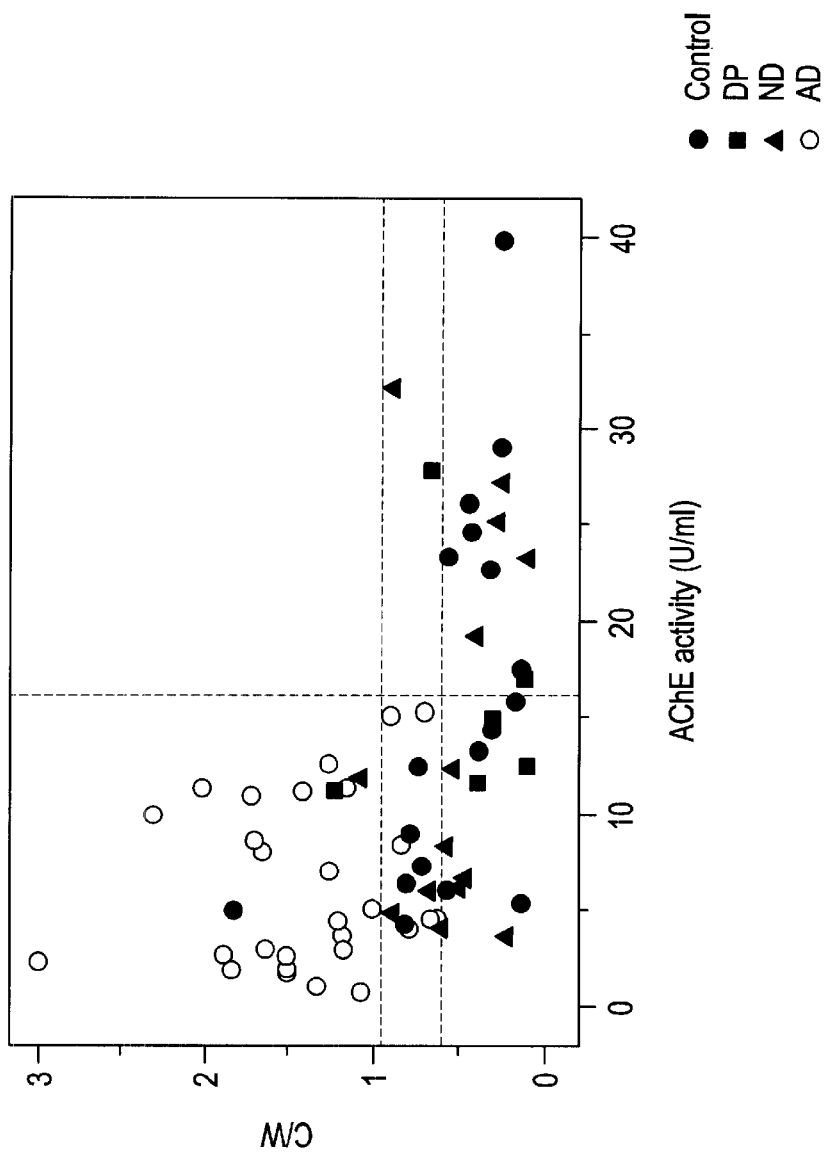
FIG. 2 is a plot of C/W ratio vs. AChE activity in post mortem human CSF. Dashed lines show values of C/W and AChE activity which maximally discriminate between AD and non-AD groups. ND refers to individuals with various neurological diseases, including non-AD type dementia, and DP refers to individuals who have no clinical signs of dementia, but who have a moderate number of non-neuritic Ab-immunoreactive diffuse plaques. Approximately 80% of all AD samples were above a cutoff value of C/W=0.95, whereas all AD samples were above C/W=0.60. Similarly all AD samples had less than 15.8 U/ml of AChE activity. The experiment is described in Example 2.

There was a small but significant difference in the binding of AChE to Con A and WGA between the AD group and controls (Table 1). As the percentage of AChE unbound in the AD CSF was increased for Con A and decreased for WGA, a ratio (C/W=[% AChE that does not bind to Con A]/[% AChE that does not bind to WGA]) was defined, which provided greater discrimination between the two groups (Table 1). Using this method, it was found that the mean C/W ratio for the AD group was significantly greater than for the other control groups, including cases with diffuse plaques (non-demented, DP), and patients with other neurological and neuropsychiatric diseases (ND) (FIG. 2), consistent with the results shown in Example 1. Of the 30 CSF samples from confirmed AD cases, 24 samples were above a cut-off value of C/W=0.95 (FIG. 2). Only one sample from 18 controls, one out of 6 samples from cases with diffuse plaques, and one out of 14 samples from the other neurological diseases group, a frontal lobe dementia case, were above this value. The 6 AD samples with C/W ratios lower than 0.95 had C/W ratios>0.60, a value higher than the C/W mean of the non-AD groups (control= 0.53±0.1; DP=0.46±0.2; ND=0.53±0.1).

No correlation could be found between the C/W ratio and the PMI that could suggest that different C/W ratio in the AD group was due to differences in PMI. Furthermore, there was no significant difference in the PMI between the AD (33±6 hr) and non-AD samples (40±6 hr).

CSF samples were additionally analysed for total AChE activity (FIG. 2). As previously reported (Appleyard et al., 1983; Atack et al., 1988), the CSF from patients with AD had significantly lower AChE activity (6.5±0.8 U/ml) than controls (15.8±2.9 U/ml) or patients with other diseases (12.4±2.4 U/ml). However, the C/W ratio was a more reliable index of clinical status than the total level of AChE activity in the CSF (FIG. 2).

AChE Isoforms in CSF

Figure 3:
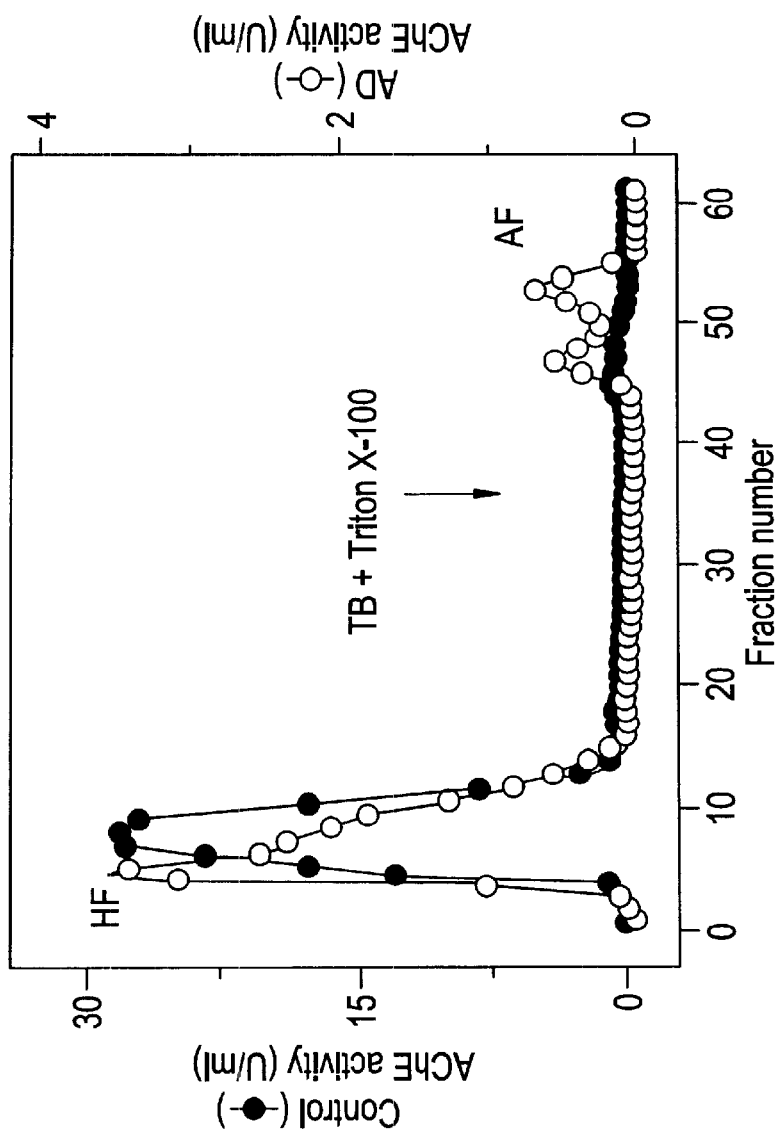
FIG. 3 shows AChE activity vs fraction number for hydrophobic interaction chromatography of CSF AChE on phenyl-agarose. Samples of CSF from AD patients (open circles) or controls (closed circles) were applied to 10 ml columns of phenyl-agarose. Hydrophilic AChE isoforms (HF) were eluted with 50 mM Tris-saline buffer and then bound amphiphilic isoforms (AF) were eluted with 50 mM Tris-HCl (TB) (pH 7.4) containing 2% (w/v) Triton X-100. Fractions of 1.4 ml were collected and assayed for AChE activity.
Figure 4:
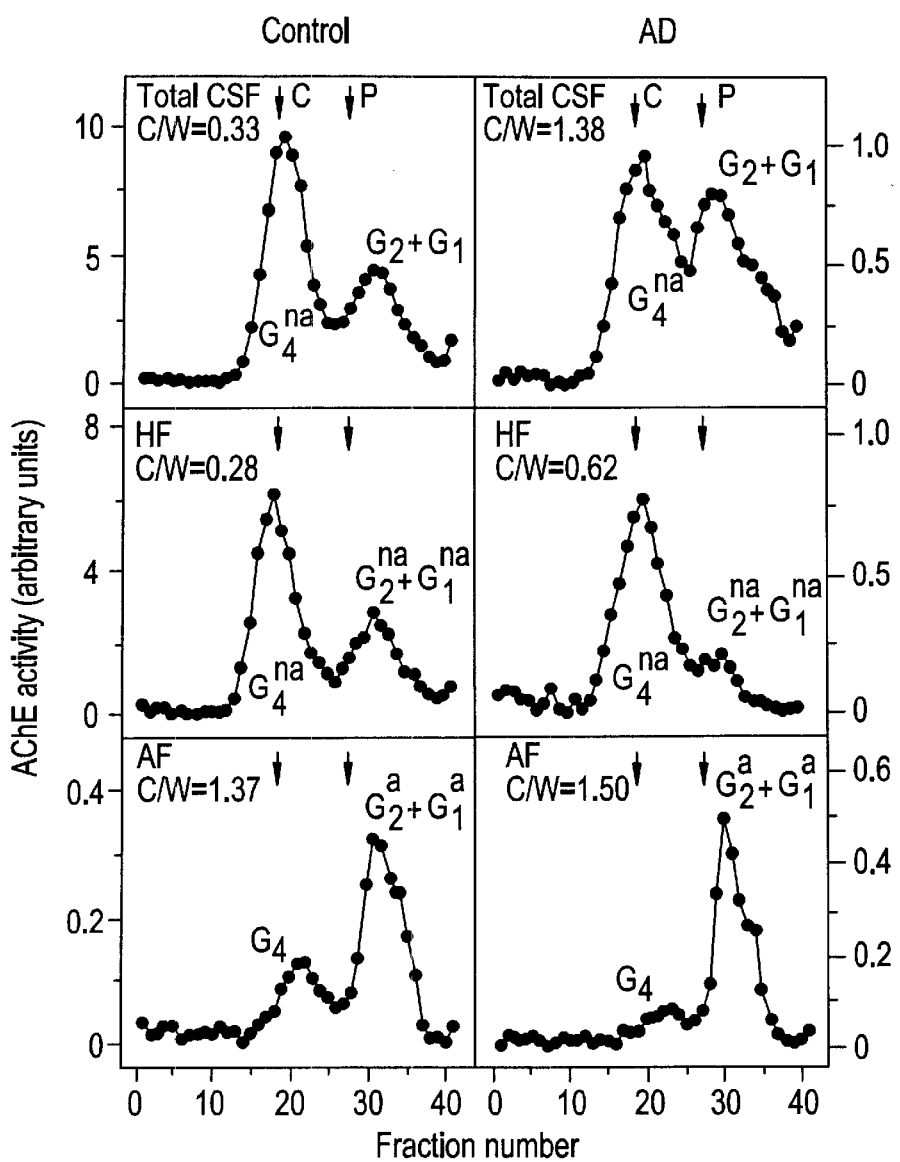
FIG. 4 is an analysis of AChE isoforms and glycosylation in AD and control CSF. A hydrophilic fraction (HF) and an amphiphilic fraction (AF) were obtained from a total CSF fraction by hydrophobic interaction chromatography (FIG. 2). $G_1$, $G_2$, and $G_4$ refer to monomer, dimer, and tetramer isoforms of AChE, respectively. $G^a$ and $G^{na}$ refer to the amphiphilic and hydrophilic AChE species, respectively. The C/W ratio in the total CSF, HF and AF fractions was determined, and then fractions were applied to 5–20% sucrose density gradients containing 0.5% (w/v) Brij 97 and centrifuged at 150,000×g for 18 hr. Fractions from the sucrose gradient were collected and assayed for AChE activity. Enzymes of known sedimentation coefficient, catalase (C, 11.4S) and alkaline phosphatase (P, 6.1S) were used to determine the approximate sedimentation coefficients of AChE isoforms.

To determine whether the alteration in glycosylation was due to changes in a specific isoform of AChE, CSF samples were analyzed by hydrophobic interaction chromatography to separate amphiphilic ($G^a$) and hydrophilic species ($G^{na}$) (FIG. 3), and by sucrose density gradient centrifugation in 0.5% (w/v) Brij 97 to separate individual molecular weight isoforms ($G_4$, $G_2$ and $G_1$) (FIG. 3). A decrease in the proportion of $G_4$ AChE in AD CSF compared to controls (FIG. 4, top panels) was observed. The ratio of ($G_4/(G_2+G_1)$) was significantly (P<0.01) higher in controls (1.80±0.12; n=4) than in AD cases (1.16±0.12; n=4). To separate hydrophilic isoforms from amphiphilic isoforms, CSF was fractionated by hydrophobic interaction chromatography on phenyl-agarose (FIG. 3). A smaller percentage of AChE in the normal CSF bound to phenyl-agarose (12±3 %, n=4) than in the AD CSF (38±4%, n=4; P<0.001). Sedimentation analysis of the unbound hydrophilic fraction (HF) showed a main peak of 10.8S, consistent with a hydrophilic tetrameric ($G_4^{na}$) isoform (Atack et al., 1987), as well as a small amount of lighter AChE isoforms, 5.1S dimers and 4.3S monomers (FIG. 4). The bound amphiphilic fraction from the phenyl-agarose column contained a minor peak of 9.0–9.5S (probably an amphiphilic tetramer, $G_4^a$) and a major peak of amphiphilic globular dimer ($G_2^a$, 4.2S) and monomer ($G_1^a$, 3.1S). The level of the amphiphilic light isoforms was greater in the AD CSF than in controls (FIG. 4).

Glycosylation of Individual AChE Isoforms in CSF

Incubation of the HF and AF with immobilised Con A and WGA showed that there was an increase in the C/W ratio in AD CSF, and that the high C/W ratio was associated with an amphiphilic fraction containing dimers and monomers (FIG. 4). The data indicate that the contribution of $G_2$ and $G_1$ AChE in AD CSF was mainly responsible for the increased C/W ratio of total AChE in the AD CSF.

Levels of AChE in Frontal Cortex and Cerebellum

To determine whether the changes in AChE glycosylation reflect a change in the expression or glycosylation of brain AChE isoforms, the levels of AChE activity in samples of frontal cortex and cerebellum were examined. Samples were homogenised with salt and Triton X-100 to extract soluble and membrane-bound AChE isoforms, and then the AChE activity determined in both fractions (Table 2). The frontal cortex samples from AD patients had significantly less AChE activity in the Triton X-100-soluble (TS) fraction (~40%), with no difference in levels in the salt-soluble (SS)

fraction compared with controls (Table 3). The results are consistent with previous studies that indicate that the major $G_4$ isoform is decreased only in the TS fraction (Younkin et al., 1986; Siek et al., 1990). A small but significant decrease (~15%) in the protein content of the TS fraction of both AD and ND groups was also observed. The level of AChE in the frontal cortex samples of the ND group was significantly different from controls in both the SS and TS fraction (Table 2). However, as the ND group was heterogeneous (2 frontal lobe dementia, 1 Huntington's disease and 1 Parkinson's disease), the significance of changes in AChE levels is unclear. Levels of AChE in cerebellum were also significantly decreased in the TS fraction from the AD group (Table 2).

Glycosylation of Frontal Cortex and Cerebellar AChE

To determine whether different glycosylation pattern of AChE in AD CSF is also present in the AD brain, the glycosylation of brain AChE was examined by lectin binding. Homogenates from frontal cortex and cerebellum were incubated with immobilised Con A or WGA and the amount of activity unbound was calculated. In the AD frontal cortex, the % AChE activity that did not bind to Con A or WGA was significantly different from controls (Table 3). Similar to the CSF AChE, the C/W ratio of frontal cortex AChE was greater in AD than in non-AD samples (Table 3). This increase was due to a large increase in the amount of AChE that did not bind to Con A, and was in spite of an increase in the amount of AChE that did not bind to WGA (Table 3). There was no increase in the C/W ratio in the DP and ND group (Table 3). No difference in lectin binding was observed between AD and non-AD groups in the cerebellar fractions (Table 3).

AChE Isoforms in Frontal Cortex and Cerebellum

Figure 5:
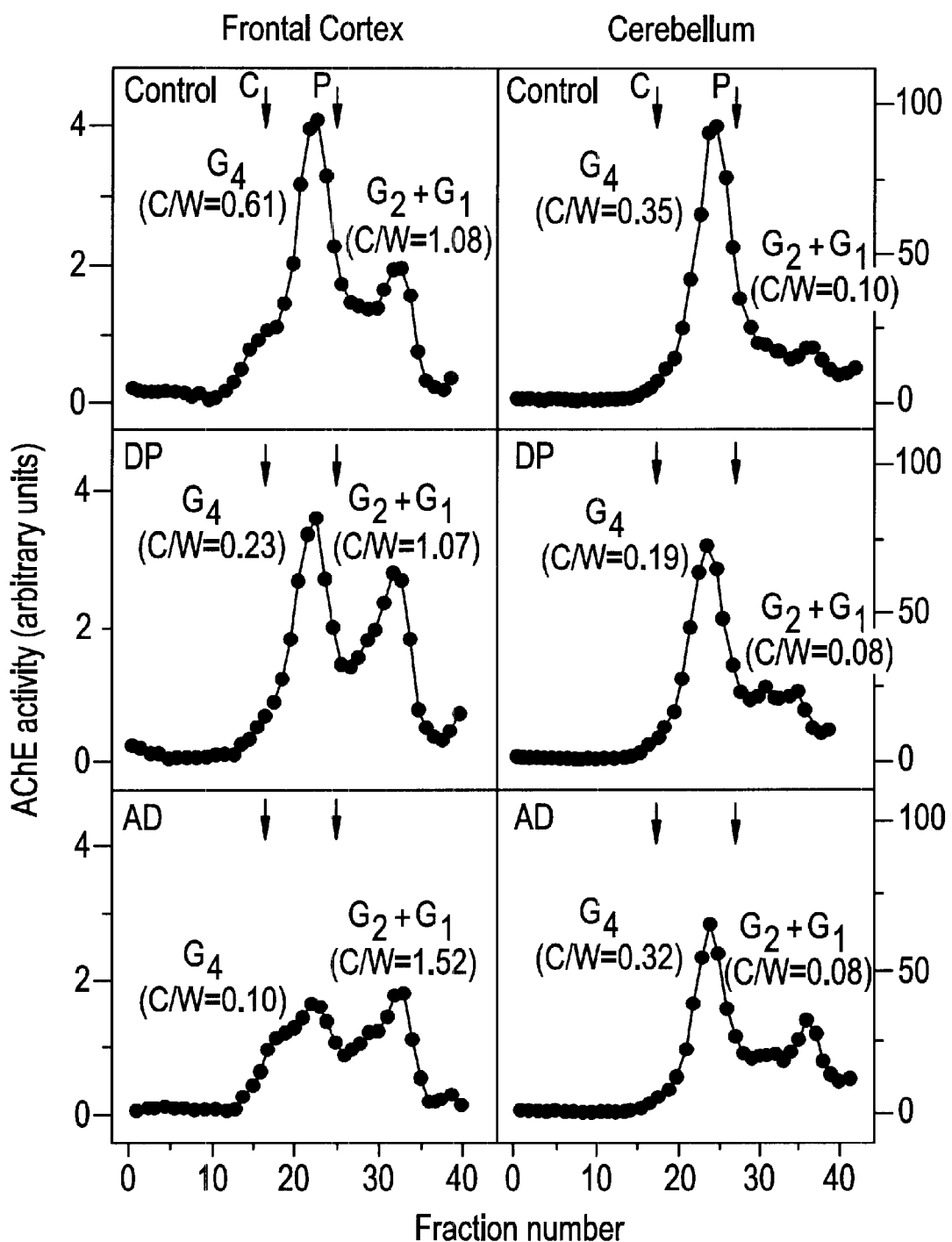
FIG. 5 is an analysis of AChE isoforms and glycosylation in frontal cortex and cerebellum from controls, non-demented individuals with diffuse plaques (DP) and AD patients. Samples of brain were homogenised and extracted to obtain SS and TS fractions. Equal volumes of SS and TS fractions were mixed and applied to 5–20% sucrose density gradients containing 0.5% (w/v) Brij 97 and centrifuged at 150,000×g for 18 hr. Fractions were collected and assayed for AChE activity. Individual AChE isoforms were identified by its coefficient of sedimentation using enzyme markers: catalase (C, 11.4S) and alkaline phosphatase (P, 6.1S). The enzyme peaks of $G_4$ and $G_2+G_1$ AChE were selected, concentrated and dialysed to remove sucrose. The major $G_4$ and $G_2+G_1$ peaks were then analysed by lectin binding using Con A and WGA and the C/W ratio determined from each peak.
Figure 6:
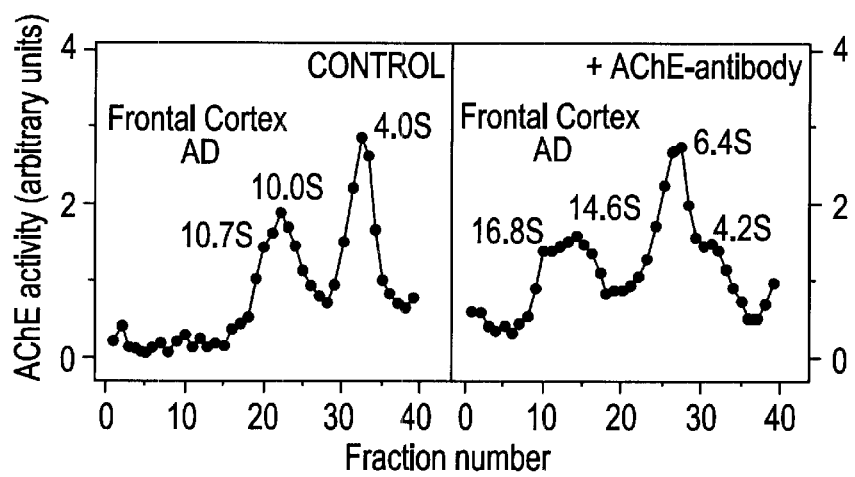
FIG. 6 shows the effect of monoclonal antibody MA3-042 on the sedimentation velocity of AChE isoforms from human frontal cortex, as described in Example 3. AD refers to Alzheimer's disease.

To determine the cause of the altered glycosylation in AD brain, the pattern of AChE isoforms in the frontal cortex and cerebellum was examined. Equal volumes of SS and ST supernatants (total AChE activity) were pooled and then analysed by sucrose density gradient sedimentation with 0.5% (w/v) Brij 97 to separate the major AChE isoforms (FIG. 5). Based on their sedimentation coefficients (Atack et al., 1986; Massoulie et al., 1982) it was possible to identify hydrophilic ($G_4^{na}$, 10.7±0.1S) and amphiphilic tetramers ($G_4^a$, 8.6±0.1S), amphiphilic dimers ($G_2^a$, 4.7±0.1S) and monomers ($G_4^a$, 3.0±0.1S) of AChE (FIG. 6). There were no differences in the sedimentation coefficient (S) of individual isoforms from each group. Due to the overlap in the sedimentation coefficients between AChE $G_4^{na}$ and $G_4^a$, it was not possible to separate these isoforms completely (FIG. 5). However, the contribution of $G_4^a$ was greater than $G_4^{na}$. Asymmetric ($A_{12}$) AChE isoforms were identified in trace amounts (2–5%) in some of the fractions.

A significant decrease in $G_4$ (40% of the mean control value, P<0.001) and in $G_2+G_1$ AChE (60% of the mean control value, P=0.002) was detected in the fractions from AD frontal cortex. This change in the relative proportion of AChE isoforms was reflected in the $G_4/(G_2+G_1)$ ratio, which was significantly lower in the AD samples (Table 3). Interestingly, a similar and statistically significant decrease was found in the $G_4/(G_2+G3)$ ratio for the DP subjects. This change in ratio was due to a 25% increase in the level of $G_2+G_1$ and a small decrease (10%) in $G_4$ AChE, although neither change on its own was statistically significant. No variation in AChE $G_4/(G_2+G_1)$ was found in the AD cerebellum (Table 3), despite a statistically significant decrease (40%) in AChE in the TS fraction (Table 2) and in the total level of $G_4$ AChE ($G_4$ in controls=380±40 U/ml, $G_4$ in ADs=195±70 U/ml; P=0.008).

Glycosylation of Individual AChE Isoforms in Frontal Cortex and Cerebellum

Since it was found that the ratio of AChE was altered in the frontal cortex of AD patients, steps were taken to ascertain whether the increase in the C/W ratio of brain AChE was due to a change in glycosylation or in the expression of a specific isoform of AChE. Individual AChE isoforms were separated by sucrose gradient centrifugation and then fractions from the $G_4$ or $G_2+G_1$ peaks were pooled, dialysed against TSB-Triton X-100 buffer and concentrated by ultrafiltration. AChE isoforms were then assayed by lectin binding and a C/W ratio calculated for each isoform (FIG. 5).

No differences were observed in the C/W ratio of $G_4$ AChE between the AD and non-AD groups (FIG. 5). However, in all frontal cortex samples the $G_2+G_1$ fraction possessed C/W ratios >1.00, demonstrating that $G_2$ or $G_1$ AChE is glycosylated differently from the $G_4$ isoform. Moreover, the C/W ratio for $G_2+G_1$ AChE was higher in the AD group than controls or DP. Similarly, the C/W ratio of the amphiphilic fraction from CSF (containing predominantly $G_2+G_1$ AChE) was higher in the AD group than in controls (FIG. 3). There was no correlation between the $G_4/(G_2+G_1)$ ratio and the C/W ratio in the DP group in frontal cortex. In the cerebellum, no differences were observed in the C/W ratios of $G_4$ AChE or $G_2+G_1$ AChE between AD and non-AD groups (FIG. 4). The $G_2+G_1$ fractions, from both AD and non-AD cerebellar groups, had a C/W<0.50, in contrast to the same fraction from frontal cortex (C/W>1.00) indicating differences in the pattern of glycosylation of $G_2+G_1$ AChE between both brain areas.

This Example shows that AChE is glycosylated differently in the frontal cortex and CSF of AD patients compared with AChE from non-AD groups including patients with non AD-type dementias. This difference in glycosylation is due to an increase in the proportion of differentially glycosylated amphiphilic dimeric and monomeric AChE in the AD samples. The results suggest that the abnormally glycosylated AChE in AD CSF may be derived from the brain as a similar difference in glycosylation was also found in the frontal cortex of AD patients.

TABLE 1

Lectin-binding of AChE in CSF.

| | AChE unbound (%) | |
|---|---|---|
| Lectin | Control | AD |
| Con A | 5.5 ± 0.8 | 10.1 ± 1.1[b] |
| WGA | 11.3 ± 1.7 | 7.0 ± 0.6[b] |
| Can A/WGA (C/W) | 0.53 ± 0.1 | 1.37 ± 0.1[a] |
| LCA | 17.2 ± 4.2 | 15.0 ± 1.3 |
| $RCA_{120}$ | 74.1 ± 3.4 | 70.8 ± 2.7 |
| SBA | 83.0 ± 2.1 | 82.2 ± 1.9 |
| $UEA_I$ | 91.6 ± 2.2 | 87.6 ± 1.9 |
| PNA | 92.4 ± 1.7 | 92.3 ± 1.4 |
| DBA | 98.9 ± 0.8 | 95.8 ± 1.7 |

All the CSFs were taken post mortem and the diagnosis confirmed by pathological examination. CSF from normal subjects (Control group: n=18; 67±4 years at death; 11 Females/7 Males) and AD patients (AD group: n=30; 79±2 y; 15F/15M) were incubated either with an equal volume of the different immobilized lectins, and then centrifuged. AChE was assayed in the supernatant fractions. The data represent the means±SEM. [a] Significantly different (P<0.001) from the control group as assessed by Student's t test; [b] significantly different (P<0.05) from the control group as assessed by Student's t test.

TABLE 2

AChE activity and protein levels in human frontal cortex and cerebellum

| Group/Source | AChE activity (U/ml) SS | AChE activity (U/ml) TS | Protein (mg/ml) SS | Protein (mg/ml) TS |
|---|---|---|---|---|
| Control | | | | |
| Frontal Cortex (n = 11; 63 ± 5 y; 7F/4M) | 3.7 ± 0.4 | 15.1 ± 1.5 | 2.1 ± 0.1 | 2.4 ± 0.1 |
| Cerebellum (n = 7; 66 ± 5 y; 4F/3M) | 64 ± 6 | 264 ± 25 | 2.5 ± 0.1 | 1.9 ± 0.1 |
| DP | | | | |
| Frontal Cortex (n = 6; 81 ± 2 y; 4F/2M) | 5.5 ± 0.9 | 12.7 ± 1.7 | 2.1 ± 0.1 | 2.2 ± 0.1 |
| Cerebellum (n = 5; 81 ± 3 y; 3F/2M) | 49 ± 8 | 182 ± 46 | 2.6 ± 0.1 | 1.9 ± 0.1 |
| ND | | | | |
| Frontal Cortex (n = 4; 67 ± 9 y; 2F/2M) | 5.4 ± 0.6[a] | 9.3 ± 1.7[b] | 2.1 ± 0.2 | 2.0 ± 0.1[b] |
| Cerebellum (n = 2; 78 ± 14 y; 1F/1M) | 45 ± 8 | 160 ± 50 | 2.7 ± 0.2 | 2.3 ± 0.2 |
| AD | | | | |
| Frontal Cortex (n = 14; 73 ± 3 y; 8F/6M) | 3.7 ± 0.3 | 9.0 ± 0.9[a] | 2.1 ± 0.1 | 2.1 ± 0.1[a] |
| Cerebellum (n = 7; 73 ± 6 y; 5F/2M) | 48 ± 12 | 160 ± 28[b] | 2.6 ± 0.1 | 2.0 ± 0.1 |

Tissue from frontal cortex or cerebellum was homogenised and salt-soluble (SS) and Triton X-100-soluble (TS) extracts obtained. The extracts were then assayed for AChE and protein.
DP = non-demented subjects with diffuse plaques;
ND = individuals with other neurological diseases and dementias of non-AD type;
AD = individuals with Alzheimer's disease.
F = female;
M = male;
y = age in years.
Values are means ± SEM.
[a]Significantly different (P < 0.005) from the control group as assessed by Student's t test;
[b]significantly different (P < 0.05) from the control group as assessed by Student's t test.

TABLE 3

Lectin binding and AChE isoforms in frontal cortex and cerebellum

| Group/Source | Lectin binding AChE unbound to Con A (%) | Lectin binding AChE unbound to WGA (%) | C/W | AChE ratio ($G_4/G_2 + G_1$) |
|---|---|---|---|---|
| Control | | | | |
| Frontal Cortex (n = 11; 63 ± 5 y; 7F/4M) | 6.9 ± 0.8 | 12.3 ± 1.2 | 0.56 ± 0.03 | 1.90 ± 0.14 |
| Cerebellum (n = 7; 66 ± 5 y; 4F/3M) | 1.8 ± 0.1 | 10.7 ± 0.9 | 0.18 ± 0.02 | 3.02 ± 0.2 |
| DP | | | | |
| Frontal Cortex (n = 6; 81 ± 2 y; 4F/2M) | 7.4 ± 0.8 | 15.0 ± 1.0 | 0.50 ± 0.06 | 1.32 ± 0.12[b] |
| Cerebellum (n = 5; 81 ± 3 y; 3F/2M) | 2.9 ± 0.7 | 12.2 ± 1.3 | 0.23 ± 0.05 | 2.18 ± 0.33 |
| ND | | | | |
| Frontal Cortex (n = 4; 67 ± 9 y; 2F/2M) | 7.0 ± 0.6 | 13.2 ± 1.2 | 0.47 ± 0.05 | 2.61 ± 0.73 |
| Cerebellum (n = 2; 78 ± 14 y; 1F/1M) | 1.8 ± 0.2 | 10.1 ± 0.3 | 0.21 ± 0.10 | 2.50 ± 0.70 |
| AD | | | | |
| Frontal Cortex (n = 14; 73 ± 3 y; 8F/6M) | 13.1 ± 1.3[a] | 19.7 ± 1.4[a] | 0.66 ± 0.03[b] | 1.34 ± 0.18[b] |
| Cerebellum (n = 7; 73 ± 6 y; 5F/2M) | 2.4 ± 0.3 | 13.5 ± 2.3 | 0.19 ± 0.02 | 2.33 ± 0.49 |

SS and TS fractions from frontal cortex and cerebellum were pooled in equal volumes and then analysed by lectin binding using immobilised Con A and WGA.
The C/W ratio was calculated as defined in Table 2.
Aliquots of the supernatants (SS + TS) were also analysed by sucrose density gradient sedimentation to identify AChE isoforms.
Values are means ± SEM.
[a]Significantly different (P < 0.005) from the control group as assessed by Student's t test;
[b]significantly different (P < 0.05) from the control group as assessed by Student's t test.

EXAMPLE 3

Binding to Monoclonal Antibody MA3-042

Samples of Triton X-100 (1% w/v) solubilized AChE were incubated overnight at 4° C. without (see left panel of FIG. 6) or with (see right panel of FIG. 6) MA3-042 (dilution 1:50 by vol.). AChE isoforms were separated by centrifugation on 5–20% sucrose gradients made in 50 mM Tris saline buffer pH 7.4 containing 0.5% Triton X-100. The tube was centrifuged at 150,000×g at 4° C., fractions were collected from the bottom and assayed for AChE activity. Sedimentation markers were catalase (11.4S) and alkaline phosphatase (6.1S). As seen in FIG. 6, all of the peaks shift in the presence of MA3-042, indicating binding of the monoclonal antibody to the particular isoform represented by each peak, except that a peak remains around 4S. The difference between 4.0S and 4.2S is statistically insignificant, suggesting that the 4.2S peak represents an isoform with a modified glycosylation pattern not recognised by MA3-042. As will be appreciated by those skilled in the art, this peak represents an AChE monomer, which has a molecular weight of about 70000 kDa.

EXAMPLE 4
Analysis of Blood Using Monoclonal Antibody

Blood is collected and 1 ml of plasma or serum prepared using standard techniques. The fluid is passed across a 5 ml RCA-Agarose (RCA stands for *Ricinus communis* agglutinin) to remove butyrylcholinesterase and the amount of acetylcholinesterase activity eluting from the column is monitored using the Ellman assay and the peak 2 ml of activity collected. This material is then incubated for 10 min at ambient temperature with 50 micromolar iso-OMPA to inhibit the remaining butyrylcholinesterase, then passed across a 1 ml column of MAb MA3-042 coupled to Sepharose to remove non-specific AChE isoforms. The amount of activity eluting from the column is assayed using the Ellman assay. The amount of activity present in this fraction is greater in AD cases than in non-AD cases. There is normally less than about 40 mUnits of AChE/ml of original plasma or serum.

INDUSTRIAL APPLICABILITY

The present invention provides a diagnostic test for Alzheimer's disease.

REFERENCES

The following references are incorporated herein by reference:

Appleyard M. E. and McDonald B. (1992) Acetylcholinesterase and butyrylcholinesterase activities in cerebrospinal fluid from different levels of the neuraxis of patients with dementia of the Alzheimer type. *J. Neurol. Neurosurg. Psychiat.* 55, 1074–1078.

Appleyard M. E., Smith A. D., Berman P., Wilcock G. K., Esiri M. M., Bowen D. M. and Neary D. (1987) Cholinesterase activities in cerebrospinal fluid of patients with senile dementia of the Alzheimer Type. *Brain* 110, 1309–1322.

Appleyard M. E., Smith A. D., Wilcock G. R. and Esiri M. M. Decreased CSF acetylcholinesterase activity in Alzheimer's disease. *Lancet* 1983; 20:452.

Arendt T., Bigl V., Walther F. and Sonntag M. (1984) Decreased ratio of CSF acetylcholinesterase to butyrylcholinesterase activity in Alzheimer's disease. *Lancet i*, 173.

Arendt T., Bruckner M. K., Lange M. and Bigl V. (1992) Changes in acetylcholinesterase and butyrylcholinesterase in Alzheimer's disease resemble embryonic development—A study of molecular forms. *Neurochem. Intl.* 21, 381–396.

Atack J. R., Perry E. K, Bonham, J. R., Candy, J. M., and Perry R. H. (1986) Molecular forms of acetylcholinesterase in the aged human central nervous system. *J. Neurochem.* 47, 267–267.

Atack J. R., Perry E. K., Bonham J. R. and Perry R. H. (1987) Molecular forms of acetylcholinesterase and butyrylcholinesterase in human plasma and cerebrospinal fluid. *J. Neurochem.* 48, 1845–1850.

Atack J. R., May C., Kaye J. A., Kay A. D., and Rapoport S. I. (1988) Cerebrospinal fluid cholinesterases in aging and in dementia of the Alzheimer type. *Ann. Neurol.* 23, 161–167.

Atack J. R., Perry E. K., Bonham J. R., Perry R. H., Tomlinson B. E., Blessed G. and Fairbairn A. (1983) Molecular forms of acetylcholinesterase in senile demential of Alzheimer's type: selective loss of the intermediate (10S) form. *Neurosci. Lett.* 40, 199–204.

Atack J. R., Perry E. K., Perry R. H., Wilson I. D., Bober M. J., Blessed G. and Tomlinson B. E. (1985) Blood acetyl- and butyrylcholinesterase in senile dementia of Alzheimer type. *J. neurol. Sci.* 70, 1–12.

Blass J. P., Blennow K., Delacourte A., Frisoni G. B., Jefferies W. A., McRae A., Wisniewski H. M., Parshad R., Scinto L. F. M., Scheltens P., Riekkinen P. J., Swanwick G. R. J., Wahlund L. -O., Trojanowski J. Q., Winbland B., Ihara Y., et al. (1998) Consensus report of the Working Group on: "molecular and biochemical markers of Alzheimer's disease". *Neurobiol. Aging* 19, 109–116.

Davies C. A., Mann D. M. A., Sumpter P. Q., and Yates P. O. (1987) A quantitative morphometric analysis of the neuronal and synaptic content of the frontal and temporal cortex in patients with Alzheimer's disease. *J. Neurol. Sci.* 78, 151–164.

Ellman G. E., Courtney K. D., Andres Jr. V. and Featherstone R. M. (1961) A new and rapid colorimetric determination of acetylcholinesterase activity. *Biochem. Pharmacol.* 7, 88–95.

Fishman E. B., Siek G. C., MacCallum R. D., Bird E. D., Volicer L., and Marquis J. K. (1986) Distribution of the molecular forms of acetycholinesterase in human brain, alterations in dementia of the Alzheimer type. *Ann. Neurol.* 19, 246–252.

Friede R. L. (1965) Enzyme histochemical studies of senile plaques. *J. Neuropathol. Exp. Neurol.* 24, 477–491.

Geula C., and Mesulam M. -M. (1989) Special properties of cholinesterases in the cerebral cortex of Alzheimer's disease. *Brain Res.* 498, 185–189.

Grassi J., Vigny M., and Massoulié J. (1982) Molecular forms of acetylcholinesterase in bovine caudate nucleus and superior cervical ganglion: solubility properties and hydrophobic character. *J. Neurochem.* 38, 457–469.

Guillozet A. L., Smiley J., Hash D. C. and Mesulam M. -M. (1997) Butyrylcholinesterase in the life cicle of amyloid plaques. *Ann. Neurol.* 42, 909–918.

Hogan B., Costantini F., and Lacy E. (1986) Manipulating the Mouse Embryo, A laboratory manual, Cold Spring Habor, N.Y.

Inestrosa N. C., Alvarez A., Perez C. A., Moreno R. D., Vicente M., Linker C., Casanueva O. I., Soto C., and Garrido J. (1996a) Acetylcholinesterase accelerates assembly of amyloid-b-peptides into Alzheimer's fibrils—possible role of the peripheral site of the enzyme. *Neuron* 16, 881–891.

Inestrosa N. C., Alvarez A., and Calderon F. (1996b) Acetylcholinesterase is a senile plaque component that promotes assembly of amyloid beta-peptide into Alzheimere's filaments. Mo 1. *Psychiatry* 1, 359–361.

Kang J., Lemaire H. -G., Unterbeck A., Salbaum J. M., Masters C. L., Grzeschik K. -H., Multhaup G., Beyreuther K., and Müller-Hill B. (1987) The precursor of Alzheimer's disease amyloid A4 protein resembles a cell-surface receptor. *Nature* 325, 733–736.

Liao J., Heider H., Sun M. -C., and Brodbeck U. (1992) Different glycosylation in acetylcholinesterases from mammalian brain and erythrocytes. *J. Neurochem.* 58, 1230–1238.

Luo Z., Fuentes M. -E., and Taylor P. (1994) Regulation of acetylcholinesterase mRNA stability by calcium during differentiation from myoblasts to myotubes. *J. Biol. Chem.* 269, 27216–27223.

Mann D. M. A., Xwatsubo T., and Snowden J. S. (1996) Atypical amyloid (Ab) deposition in the cerebellum in Alzheimer's disease: an immunohistochemical study using end-specific Ab monoclonal antibodies. *Acta Neuropathol.* 91, 647–653.

Massoulié J., and Bon S. (1982) The molecular forms of cholinesterase and acetylcholinesterase in vertebrates. *Ann. Rev. Neurosci.* 5, 57–106.

Massoulie J., Pezzementi L., Bon S., Krejci B., and Vallette F. -M. (1993) Molecular and cellular biology of cholinesterases. *Prog. Neurobiol.* 41, 31–91.

Masters C. L., Simms G., Weinman N. A., Multhaup G., McDonald B. L., and Beyreuther K. (1985) Amyloid plaque core protein in Alzheimer's disease and Down syndrome. *Proc. Natl. Acad. Sci. USA* 82, 4245–4249.

Méflah K., Bernard S., and Massoulié J.(1984) Interactions with lectins indicate differences in the carbohydrate composition of the membrane-bound enzymes acetylcholinesterase and 5'-nucleotidase in different cell types. *Biochimie* 66, 59–69.

Mesulam M. -M., Geula C., and Moran M. A. (1987) Anatomy of cholinesterase inhibition in Alzheimer's disease, effect of physostigmine and tetrahydroaminoacridine on plaques and tangles. *Ann. Neurol.* 22, 683–691.

Michaelson S., and Small D. H. (1993) A protease is recovered with a dimeric form of acetylcholinesterase in fetal bovine serum. *Brain Res.* 611, 75–80.

Mirra S. S., Gearing D. W., McKeel D. W., Crain B. J., Hughes J. P., Vanbelle G., Heyman A., Ball M. J., Clark A. W., Hansen L. A., Hedreen J. C., Joachim C. L., Kim R. C., Kirkpatrick J. B., Markesbery W. R., Davis D., Martínez A. J., Miller C. A., Moossy J., Morris J., Nochlin D., Perl D. P., Purohit D., Petito C. K., Rao G. R., et al. (1994) Interlaboratory comparison neuropathology assessments in Alzheimer's disease: A study of the Consortium to Establish a Registry of Alzheimer's Disease (CERAD). *J. Neuropath. Exp. Neurol.* 53, 303–315.

Moral-Naranjo M. T., Cabezas-Herrera J., and Vidal C. J. (1996) Molecular forms of acetyl- and butyrylcholinesterase in normal and dystrophic mouse brain. *J Neurosci. Res.* 43, 224–234.

Morán M. A., Mufson E. J., and Gómez-Ramos P. (1993) Colocalization of cholinesterases with b amyloid protein in aged and Alzheimer's brains. *Acta Neuropathol.* 85, 362–369.

Motter R., Vigopeifrey C., Kholodenko D., Barbour R., Johnsonwood K., Galasko D., Chang L., Miller B., Clark C., Green R., Olson D., Southwick P., Wolfert R., Munroe B., Lieberburg I., Seubert P., and Schenk D. (1995) Reduction of b-amyloid peptide$_{42}$ in the cerebrospinal fluid of patients with Alzheimer's disease. *Ann. Neurol.* 38, 643–648.

Navaratnam D. S., Priddle J. D., McDonald B., Esiri M. M., Robinson J. R., and Smith A. D. (1991) Anomalous molecular form of acetylcholinesterase in cerebrospinal fluid in histologically diagnosed Alzheimer's disease. *Lancet* 337, 447–450.

Pfeffer R. I., Afifi A. A., and Chance J. M. (1987) Prevalence of Alzheimer's disease in a retirement community. *Am. J. Epidemial.* 125, 420–436.

Probst A., Langui D., and Ulrich J. (1991) Alzheimer's disease: a description of the structural lesions. *Brain Pathol.* 1, 229–239.

Sáez-Valero J., Tornel P. L., Muñoz-Delgado B., and Vidal C. J. (1993) Amphiphilic and hydrophilic forms of acetyl- and butyrylcholinesterase in human brain. *J. Neudosci. Res.* 35, 678–689.

Sáez-Valero J., Sberna G., McLean C., Masters C. L., and Small D. H. (1997) Glycosylation of acetyicholinesterase as diagnostic marker for Alzheimer's disease. *Lancet* 350, 929.

Saxena A., Raveh L., Ashani Y., and Doctor B. P. (1997) Structure of glycan moieties responsible for the extended circulatory life time of fetal bovine seru acetylcsolinesterase and equine serum butyrylcholinesterase. *Biochemistry* 36, 7481–7489.

Saxena A., Ashani Y., Raveh L., Stevenson D., Patel T., and Doctor B. P. (1998) Role of oligosaccharides in the pharmacokinetics of tissue-derived and genetically engineered cholinesterases. *Mol. Pharmacol.* 53, 112–122.

Sberna G., Sáez-Valero J., Beyreuther K., Masters C. L., and Small D. H. (1997) The amyloid b-protein of Alzheimer's disease increases acetylcholinesterase expression by increasing intracellular calcium in embryonal carcinoma P19 cells. *J. Neurochem.* 69, 1177–1184.

Sberna G., Sáez-Valero J., Li Q. X., Czech C., Beyreuther K., Masters C. L., McLean, C. A., and Small D. H. (1998) Acetylcholinesterase is increased in the brains of transgenic mice expressing the C-terminal fragment (CT100) of the b-amyloid protein precursor of Alzheimer's disease. *J. Neurochem.* 71, 723–731.

Schegg K. M., Harrington L. S., Nielsen S., Zwieg R. M., and Peacock J. H. (1992) Soluble and membrane-bound forms of brain acetylcholinesterase in Alzheimer's disease. Neurobiol. *Aging* 13, 697–704.

Schoenberg B. S., Kokmen B., and Okazaki H. (1987) Alzheimer's disease and other dementing illnesses in a defined United States population: incidence rates and clinical features. *Ann. Neurol.* 22, 724–729.

Shen Z. -X., and Zhang Z. (1993) Anomalous acetylcholinesterase in CSF without clinical diagnosis of Alzheimer's disease. *Lancet* 342, 62.

Shen Z. -X. (1997) An CSF anomalous molecular form of acetylcholinesterase in demented and non-demented subject. *Neuroreport* 8, 3229–3232.

Siek G. C., Katz L. S., Fishman E. B., Korosi T. S., and Marquis J. K. (1990) Molecular forms of acetyilcholinesterase in subcortical areas of normal and Alzheimer disease brain. *Biol Psychiatry* 27, 573–580.

Silman I., Lyles J. M., and Barnard E. A. (1978) intrinsic forms of acetyicholinesterase in skeletal muscle. *FEBS Letters* 94, 166–170.

Small D. H., Michaelson S., and Sberna G. (1996) Non-classical actions of cholinesterases: role in cellular differentiation, tumorigenesis and Alzheimer's disease. *Neurochem. Intl.* 28, 453–483.

Smith P. K., Krohn R. I., Hermanson G. T., Mallia A. K., Gartner F. H., Provenzano M. D., Fujimoto E. K., Goeke N. M., Olson B. J., and Klenk D.C. (1985) Measurement of protein using bicinchoninic acid. *Anal. Biochem.* 150, 76–85.

Smith A. D., Jobst K. A., Navaratnam D. S., Shen Z. -X., Priddle J. D., McDonald B., King E., and Esiri M. M.(1991) Anomalous acetylcholinesterase in lumbar CSF in Alzheimer's disease. *Lancet* 338, 1538.

Soreq H., Ben-Aziz R., Prody C. A., Seidman S., Gnatt A., Neville L., Lieman-Hurwitz J., Lev-Lehman E., Ginzberg D., Lapidot-Lifson Y., and Zakut H. (1990) Molecular cloning and construction of the coding region for human acetylcholinesterase reveals a G+C-rich attenuating structure. *Proc. Natl. Acad. Sci. USA* 87, 9688–9692.

Treskatis S., Christoph E., and Layer P. G. (1992) Butyrylcholinesterase from chicken brain is smaller than that from serum: its purification, glycosylation and membrane association. *J. Neurochem.* 58, 2236–2247.

Ulrich J., Meier-Ruge W., Probst A., Meier E., and Ipsen S. (1990) Senile plaques, staining for acetylcholinesterase and A4 protein, a comparative study in the hippocampus and entorhinal cortex. *Acta Neuropathol* 80, 624–628.

Vidal C. J. (1996) Glycosylation of cholinesterases and its alteration in some pathological states. *Recent Res. Devel. Neurochem.* 1, 37–54.

Wright C. I., Geula C., and Mesulam M. -M. (1993) Neuroglial cholinesterases in the normal brain and in Alzheimer's disease, relationship to plaques, tangles and patterns of selective vulnerability. *Ann. Neural.* 34, 373–384.

Younkin S. G., Goodridge B., Katz J., Lockett G., Nafziger D., Usiak M. F., and Younkin L. H. (1986) Molecular forms of acetylcholinesterase in Alzheimer's disease. *Fed. Proc.* 45, 2982–2988.

What is claimed is:

1. A method for the diagnosis of Alzheimer's disease (AD) in a patient, comprising the steps of:
    (1) providing a sample of an appropriate body fluid from said patient;
    (2) detecting the presence in said sample of an acetylcholinesterase (AChE) having an altered glycosylation pattern such that it has a relatively lesser affinity for Concanavalin A (Con A) and a relatively greater affinity for wheat germ agglutinin (WGA) than an AChE with an unaltered glycosylation pattern;
    (3) correlating the presence of said AChE having a glycosylation pattern such that it has a relatively lesser affinity for Con A and a relatively greater affinity for WGA than an AChE with an unaltered glycosylation pattern, with AD in said patient.

2. The method of claim 1, wherein the relative proportions of a first AChE having a glycosylation pattern such that it has a relatively lesser affinity for Con A and a relatively greater affinity for a WGA than an AChE having an unaltered glycosylation pattern, and a second AChE having an unaltered glycosylation pattern is measured.

3. The method of claim 2, wherein a lectin-binding analysis is used to measure the relative proportions of said first AChE and said second AChE.

4. The method of claim 3, wherein said lectin-binding analysis includes measurement of binding to Concanavalin A (Con A) and wheat germ agglutinin (WGA).

5. The method of claim 4, wherein activity of unbound AChE is determined.

6. The method of claim 5, wherein the ratio of AChE to Con A to AchE unbound to WGA is calculated.

7. The method of claim 6, wherein said ratio is above 0.95 in AD patients.

8. The method of claim 1, wherein the total AChE activity is also determined.

9. The method of claim 8, wherein the ratio of AChE unbound to Con A to AChE unbound to WGA is plotted against total AChE activity.

10. The method of claim 1, wherein a monoclonal antibody is used to detect the presence of said AChE having a relatively lesser affinity for Concanavalin A (Con A) and a relatively greater affinity for wheat germ agglutinin (WGA) than AChE with an unaltered glycosylation pattern.

11. The method of claim 10, wherein said monoclonal antibody is MA3-042, and said AChE having an altered glycosylation pattern such that it has a relatively lesser affinity for Con A and a relatively greater affinity for WGA than AChE having an unaltered glycosylation pattern is detected by its failure to bind to said antibody.

12. The method of claim 1, wherein an abnormal isoform of AChE having an altered glycosylation pattern such that it has a relatively lesser affinity for Con A and a relatively greater affinity for WGA than AChE having an unaltered glycosylation pattern is detected.

13. The method of claim 12, wherein said abnormal isoform is the amphiphilic, monomeric isoform of AChE or the amphiphilic, dimeric isoform of AChE.

14. The method of claim 1, wherein said body fluid is cerebrospinal fluid (CSF), blood or blood plasma.

15. The method of claim 14, wherein said body fluid is blood and blood plasma is prepared from the blood for analysis.

16. The method of claim 14, wherein said body fluid is blood plasma and butyrylcholinesterase (BChE) is removed or inactivated prior to analysis for the presence of AChE with an altered glycosylation pattern.

17. An isolated and purified abnormal isoform of acetylcholinesterase (AChE) with an altered glycosylation pattern, being the amphiphilic, monomeric isoform of AChE, which has a relatively lesser affinity for Concanavalin A (Con A) and a relatively greater affinity for wheat germ agglutinin (WGA) than AChE with an unalterated glycosylation pattern.

18. An isolated and purified abnormal isoform of acetylcholinesterase (AChE) with an altered glycosylation pattern, being the amphiphilic, dimeric isoform of AChE, which has a relatively lesser affinity for Concanavalin A (Con A) and a relatively greater affinity for wheat germ agglutinin (WGA) than AChE with an unaltered glycosylation pattern.

* * * * *